(12) United States Patent
Dyer et al.

(10) Patent No.: US 7,662,403 B2
(45) Date of Patent: Feb. 16, 2010

(54) PHARMACEUTICAL FORMULATIONS FOR INTRANASAL ADMINISTRATION OF PROTEIN COMPRISING A CHITOSAN OR A DERIVATIVE THEREOF

(75) Inventors: Ann Margaret Dyer, Nottingham (GB); Peter James Watts, Nottingham (GB); Yu-Hui Cheng, Nottingham (GB); Alan Smith, Nottingham (GB)

(73) Assignee: Archimedes Development Limited, Nottingham (GB)

( * ) Notice: Subject to any disclaimer, the term of this patent is extended or adjusted under 35 U.S.C. 154(b) by 0 days.

(21) Appl. No.: 11/325,073

(22) Filed: Jan. 4, 2006

(65) Prior Publication Data

US 2006/0120973 A1  Jun. 8, 2006

Related U.S. Application Data

(63) Continuation of application No. PCT/GB2004/002876, filed on Jul. 2, 2004.

(30) Foreign Application Priority Data

Jul. 4, 2003  (GB) ................. 0315632.0

(51) Int. Cl.
*A61K 9/14* (2006.01)
*A61K 38/00* (2006.01)
*A61K 38/27* (2006.01)
*A61M 11/00* (2006.01)

(52) U.S. Cl. .............. 424/434; 424/489; 424/499; 514/2; 514/951

(58) Field of Classification Search ........... 424/434, 424/489, 499; 514/2, 951
See application file for complete search history.

(56) References Cited

U.S. PATENT DOCUMENTS

| | | | | |
|---|---|---|---|---|
| 5,840,341 | A * | 11/1998 | Watts et al. | ............ 424/499 |
| 5,863,554 | A | 1/1999 | Illum | |
| 6,391,318 | B1 | 5/2002 | Illum | |
| 2001/0053359 | A1 | 12/2001 | Illum | |
| 2005/0271728 | A1 * | 12/2005 | Nomura et al. | ............ 424/487 |

FOREIGN PATENT DOCUMENTS

| | | | |
|---|---|---|---|
| EP | 0 943 326 A1 | 9/1999 | |
| JP | 07-118170 | * | 5/1995 |
| WO | WO 90/09780 A1 | 9/1990 | |
| WO | WO 96/05810 A1 | 2/1996 | |
| WO | WO 96/10421 A1 | 4/1996 | |
| WO | WO 9620730 | * | 7/1996 |
| WO | WO 97/16208 A1 | 5/1997 | |
| WO | WO 97/20576 A1 | 6/1997 | |
| WO | WO 98/01160 A2 | 1/1998 | |
| WO | WO 98/01161 A2 | 1/1998 | |
| WO | WO 9830207 | * | 7/1998 |
| WO | WO 99/01498 A1 | 1/1999 | |
| WO | WO 99/27960 A1 | 6/1999 | |
| WO | WO 03/043574 A2 | 5/2003 | |

OTHER PUBLICATIONS

Lacy et al, Drug Information Handbook, 1993, pp. 436-437.*
Aspden et al, Journal of Pharmaceutical Sciences, vol. 86, No. 4, Apr. 1997, pp. 509-513 (XP 000683471).*
Illum et al., "Nasal drug delivery—possibilities, problems and solutions", *Journal of Controlled Release*, vol. 87, pp. 187-198 (2003).
Aspden et al., "Chitosan as a nasal delivery system: Evaluation of the effect of chitosan on mucociliary clearance rate in a frog palate model", *International Journal of Pharmaceutics*, vol. 122, pp. 69-78 (1995).
Illum et al., "Chitosan as a Novel Nasal Delivery System for Peptide Drugs", *Pharmaceutical Research*, vol. 11, pp. 1186-1189 (1994).
Davis et al., "Absorption Enhancers for Nasal Drug Delivery", *Clinical Pharmacokinetics*, vol. 42, pp. 1107-1128 (2003).
Martindale (The Complete Drug Reference), $33^{rd}$ edition, *Pharmaceutical Press*, London, pp. 1291 and 750 (2002).
Illum et al., "Novel chitosan-based delivery systems for the nasal administration of a LHRH-analogue", *STP Pharma Sciences*, vol. 10, pp. 89-94 (2000).
Illum, "Nasal drug delivery: new developments and strategies", *Drug Discovery Today*, vol. 7, pp. 1184-1189 (2002).
Rouan, "Developments in Protein Drug Delivery," *Modern Pharmaceutics*, pp. 866-867, $3^{rd}$ Edition, Banker and Rhodes (eds.), Marcel Dekker, New York (1996).
Winters et al., "Precipitation of Proteins in Supercritical Carbon Dioxide", *Journal of Pharmaceutical Sciences*, vol. 85, pp. 586-594 (1996).
Subramaniam et al., "Pharmaceutical Processing with Supercritical Carbon Dioxide", *Journal of Pharmaceutical Sciences*, vol. 86, pp. 885-890 (1997).
Palakodaty et al., "Phase Behavioral Effects on Particle Formation Processes Using Supercritical Fluids", *Pharmaceutical Research*, vol. 16, pp. 976-985 (1999).
Nucci et al., "The therapeutic value of poly(ethylene glycol)-modified proteins", *Advanced Drug Delivery Reviews*, vol. 6, pp. 133-151 (1991).
Roberts, "Chitin Chemistry", Macmillan Press Ltd., London (1992)—too Voluminous to Include.
Carstensen, Ph.D., "Powder Dosage Forms, Densities and Blending", *Pharmaceutical Principles of Solid Dosage Forms*, Chapters 2 and 6, Technomic Publishing Co., Inc., Lancaster, PA (1993).
O'Connor, Ph.D., "Powders", *Remington: The Science and Practice of Pharmacy*, $20^{th}$ Ed., Chapter 37, Lipincott, Williams and Wilkins, Baltimore (2000).

(Continued)

*Primary Examiner*—Mina Haghighatian
(74) *Attorney, Agent, or Firm*—Panitch Schwarze Belisario & Nadel LLP

(57) ABSTRACT

There is provided a powder formulation for nasal delivery including a protein having a molecular weight of 10 kDa or greater and chitosan or a derivative thereof or a salt of chitosan or a salt of a derivative of chitosan. Preferably the protein is human growth hormone.

23 Claims, 3 Drawing Sheets

OTHER PUBLICATIONS

Broadhead et al., "The Spray Drying of Pharmaceuticals", *Drug Development and Industrial Pharmacy*, vol. 18, pp. 1169-1206 (1992).

"Handbook of Pharmaceutical Excipients", 4th Ed., Pharmaceutical Press, London, Rowe et al. (eds) (2003)—Table of Contents only.

"Goodman & Gilman's The Pharmacological Basis of Therapeutics", 9th Ed., McGraw-Hill, New York (1995)—Table of Contents only.

Hinchcliffe et al., "Intranasal insulin delivery and therapy", *Advanced Drug Deliver Reviews*, vol. 35, pp. 199-234 (1999).

\* cited by examiner

Larger Particles

PHARMACEUTICAL FORMULATIONS FOR INTRANASAL ADMINISTRATION OF PROTEIN COMPRISING A CHITOSAN OR A DERIVATIVE THEREOF

CROSS-REFERENCE TO RELATED APPLICATIONS

This application is a continuation of International Application No. PCT/GB2004/002876, filed Jul. 2, 2004, which was published in the English language on Jan. 20, 2005, under International Publication No. WO 2005/004838 A1, and the disclosure of which is incorporated herein by reference.

BACKGROUND OF THE INVENTION

This invention relates to pharmaceutical formulations for the intranasal administration of proteins.

It is now possible to manufacture well-defined, highly purified proteins on a large scale. This has revolutionized many areas of medicine. However, these proteins, without exception, currently have to be administered by injection because they are inadequately absorbed by the body when administered by other routes.

It would be highly desirable to administer high molecular weight proteins by a non-injected route in order to improve patient acceptability, compliance and convenience.

The nasal route has been successfully used for the administration of a number of peptide drugs. Simple aqueous solution formulations for the nasal administration of peptides including desmopressin (molecular weight 1.1 kDa), salmon calcitonin (3.5 kDa) and LHRH analogues such as nafarelin (1.3 kDa) are on the market. It should be noted, however, that the bioavailability of peptides from these formulations is generally low. For example, the reported nasal bioavailability (relative to the injection route) in humans of nafarelin and salmon calcitonin is around 3% (Martindale, *The Extra Pharmacopoeia*, 33$^{rd}$ edition, Pharmaceutical Press, London, pages 1291 and 750 (2002)).

Formulations for intranasal delivery containing selected peptide and low molecular weight protein drugs, such as insulin (molecular weight 5.8 kDa), leuprolide (1.3 kDa), goserelin (1.3 kDa), salmon calcitonin and parathyroid hormone (1-34) (4.2 kDa) have also been reported (International application publication No. WO 90/09780; Illum et al., *Pharmaceutical Research*, 11:1186-1189 (1994); Illum et al., *STP Pharma Sciences*, 10:89-94 (2000); Illum, *Drug Discovery Today*, 7:1184-1189 (2002); Illum, *J. Control. Rel*, 87:187-198 (2003); and European published patent application EP 943 326 A1).

The nasal route of delivery has not, however, proved successful for larger proteins with molecular weights in excess of 10 kDa (Rouan, *Modern Pharmaceutics*, 3$^{rd}$ Edition, Chapter 22, pp. 866-867, Banker and Rhodes (eds), Marcel Dekker, New York (1996)).

The listing or discussion of a prior-published document in this specification should not necessarily be taken as an acknowledgement that the document is part of the state of the art or is common general knowledge.

There remains a need for alternative means for the delivery of proteins having a molecular weight of 10 kDa or greater.

BRIEF SUMMARY OF THE INVENTION

The present invention provides a formulation suitable for the intranasal administration of proteins having a molecular weight of 10 kDa or greater.

We have surprisingly found that the intranasal administration of proteins having a molecular weight of 10 kDa or greater can be achieved using a powder formulation comprising the protein and chitosan or a derivative thereof or a salt of chitosan or a salt of a derivative of chitosan. Effective absorption of the protein can be achieved using such a formulation.

The present invention provides a powder formulation for intranasal delivery comprising a protein having a molecular weight of 10 kDa or greater and chitosan or a derivative thereof or a salt of chitosan or a salt of a derivative of chitosan. The formulations of the present invention preferably contain chitosan or a derivative thereof or a salt of chitosan or a salt of a derivative of chitosan in an amount of about 20 to 80% by weight, more preferably about 25 to 70% by weight and most preferably about 30 to 65% by weight. The remainder of the powder formulation comprises protein and, optionally, other ingredients to improve product stability and/or handling properties, such as powder flow. The protein content of the powder formulation is preferably about 15 to 75% by weight, more preferably about 25 to 70% and most preferably about 30 to 65%.

Proteins suitable for use in the present invention are those having a molecular weight of 10 kDa or greater. Preferably the proteins have a molecular weight of about 10 to 100 kDa, more preferably about 10 to 60 kDa and most preferably about 10 to 40 kDa.

Typically, the proteins used in the present invention are those that have a therapeutic or prophylactic effect. Preferably, the proteins used in the present invention are those that are absorbed into systemic circulation through the nasal mucosa and which have a direct and/or systemic biological effect following absorption. In this respect, protein drugs which have a local effect when administered to the nasal mucosa, as well as vaccines, are excluded from the scope of the present invention.

The present invention also provides processes for preparing the powder formulations described above.

The present invention also provides the use of chitosan or a derivative thereof or a salt of chitosan or a salt of a derivative of chitosan in the manufacture of an hGH-containing powder formulation for nasal administration for the treatment or prevention of growth retardation, for example the growth retardation caused by insufficient growth hormone secretion, Turner's syndrome or chronic renal insufficiency; for the treatment or prevention of growth hormone deficiency; or for the control of HIV-related wasting and cachexia.

The present invention also provides a nasal delivery device such as a spray device or a dose cartridge for use with such a device loaded with a formulation as described above. Typically the spray device or dose cartridge will contain a single dose of the formulation, which is typically about 5 to 20 mg of the powder formulation. A typical dosing regimen would be in the range of the administration of one dose into a single nostril to the administration of two doses into each nostril.

The present invention also provides for the use of chitosan or a derivative thereof or a salt of chitosan or a salt of a derivative of chitosan to enhance the intranasal absorption of a protein having a molecular weight of 10 kDa or greater such as hGH.

The present invention also provides the use of chitosan or a derivative thereof or a salt of chitosan or a salt of a derivative of chitosan in the manufacture of a powder formulation for nasal administration of a protein having a molecular weight of 10 kDa or greater such as hGH.

The present invention further provides a method of administering a protein having a molecular weight of 10 kDa or greater such as hGH, which comprises administering a formulation of the invention to the patient via the nasal route.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
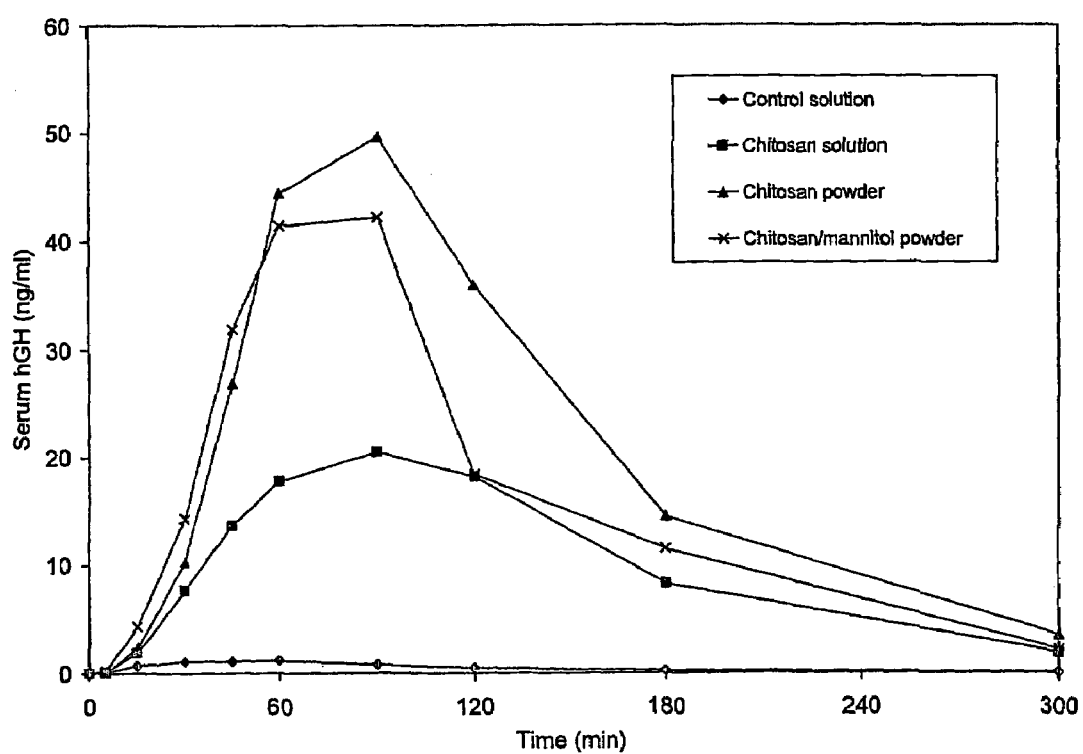
FIG. 1 is a graph showing mean hGH serum concentration vs. time curves following intranasal administration of powder and solution formulations (obtained by way of Example 6) to sheep (mean, n=5)

The term "protein" is intended to include, but is not necessarily limited to, polypeptides, glycoproteins, metalloproteins, lipoproteins and sub-units or fragments thereof. Suitable proteinaceous materials include their derivatives with; for example, polyethylene glycol. Conjugates of PEG and protein are described in Nucci et al., *Advances in Drug Delivery Reviews*, 6:113-151 (1991).

Examples of suitable proteins include, but are not limited to, blood factors such as Factor VIII (80-90 kDa); therapeutic enzymes such as P-glucocerebrosidase (60 lDa); hormones such as human growth hormone (somatropin) (22.1 kDa); erythropoetin (a glycosylated protein with molecular weight of 30.4 kDa); interferons such as interferon alfacon-1 (19.4 kDa), interferon alfa-2b (19.2 kDa), peginterferon alfa-2b (31 kDa), interferon beta-1a (22.5 kDa), interferon beta-1b (18.5 kDa) and interferon gamma-1b (16.5 kDa); colony stimulating factors such as granulocyte colony stimulating factor (G-CSF, filgrastim) (18.8 kDa), pegfilgrastim (39 kDa) and granulocyte-macrophage colony stimulating factor (GM-CSF, molgramostim, sargramostim)(14-20 kDa); interleukins such as interleukin-11 (19 kDa), recombinant forms of interleukin-2, such as aldesleukin (15.3 kDa), and interleukin-1 receptor antagonist (anakinra)(17.3 kDa); and monoclonal antibodies, such as infliximab.

The proteins to be used in the present invention may be manufactured by recombinant DNA technology. Proteins manufactured in this way are typically isolated and purified as an aqueous solution. In the present invention, the protein is used in the form of a powder.

Protein powders may be formed from protein solutions using any suitable method known in the art. Suitable methods include, but are not limited to, freeze-drying (lyophilization), spray drying, air drying, vacuum drying and supercritical fluid technology. The preferred means for isolating the protein in the form of a powder is by freeze-drying from an aqueous solution.

The protein can be dried alone or, to improve stability, in the presence of an additive. Suitable additives include, but are not limited to, buffer salts such as phosphate, citrate and acetate buffers; sugars such as sucrose and trehalose; surfactants such as polysorbates; amino acids such as glycine; polyols such as mannitol and sorbitol; and polyethylene glycols. It is preferable to dry the protein in the presence of an additive.

By the term "protein powder" we mean a powder consisting of a protein and optionally an additive but not comprising chitosan or a derivative thereof or a salt of chitosan or a salt of a derivative of chitosan.

The dry protein powder preferably comprises at least about 40% by weight, more preferably at least about 50% and most preferably at least about 60% by weight protein.

The dry protein powder preferably has a particle size in the range of about 10 to 900 μm, more preferably about 10 to 600 μm and most preferably about 10 to 300 μm. More specifically, the mean particle size, expressed as the volume mean diameter ($D_{50\%}$) and measured by a technique such as light microscopy combined with image analysis lies within these ranges. The $D_{50\%}$ is preferably about 25 to 700 μm, more preferably about 25 to 450 μm and most preferably about 25 to 200 μm. Furthermore, no more than 10% by volume of the particles have a diameter ($D_{10\%}$) less than 10 μm and at least 90% by volume of the particles have a diameter ($D_{90\%}$) that does not exceed the upper limit of the size range.

Most preferably, the protein powder is obtained by freeze-drying and comprises at least about 60% by weight of protein and has a mean particle size, expressed as the volume mean diameter ($D_{50\%}$) of about 25 to 200 μm.

Chitosan is a bioadhesive cationic biopolymer comprising glucosamine and N-acetyl glucosamine: It is prepared by the deacetylation of chitin. By the term "chitosan" we include all derivatives of chitin, or poly-N-acetyl-D-glucosamine, including polyglucosamines and oligomers of glucosamine materials of different molecular weights, in which the greater proportion of the N-actyl groups have been removed through hydrolysis (deacetylation). In accordance with the present invention, the degree of deacetylation, which represents the proportion of N-acetyl groups which have been removed through deacetylation, should preferably be about 40 to 97%, more preferably about 60 to 96% and most preferably about 70 to 95%.

The chitosan, chitosan derivative or salt used in the present invention should preferably have a molecular weight of about 10,000 to 1,000,000 Da, more preferably about 15,000 to 750,000 Da and most preferably about 20,000 to 650,000 (e.g. 500,000) Da.

Pharmaceutically acceptable salts of chitosan and derivatives of chitosan are suitable for use in the present invention. Salts with various organic and inorganic acids are suitable. Such suitable salts include, but are not limited to, hydrochloride, lactate, citrate, glutamate, nitrate, phosphate and acetate. Preferred salts are chitosan glutamate and chitosan hydrochloride. The most preferred salt is chitosan glutamate.

Chitosan derivatives are also suitable for use in this invention. Suitable chitosan derivatives include, without limitation, esters, ethers or other derivatives formed by bonding acyl and/or alkyl groups with the hydroxyl groups, but not the amino groups of chitosan. Examples include O-alkyl ethers of chitosan and O-acyl esters of chitosan. Modified chitosans, such as those conjugated to polyethylene glycol may be used in the present invention. Conjugates of chitosan and polyethylene glycol are described in International patent application publication No. WO 99/01498.

It is preferable that the chitosan, chitosan derivative or salt used in the present invention is water soluble. Chitosan glutamate is water soluble. By "water soluble" we mean that the chitosan, chitosan derivative or salt dissolves in water at an amount of at least 10 mg/ml at room temperature and atmospheric pressure.

Chitosans suitable for use in the present invention may be obtained from various sources, including Primex, Haugesund, Norway; NovaMatrix, Drammen, Norway; Seigagaku America Inc., MD, USA; Meron (India) Pvt, Ltd., India; Vanson Ltd, Virginia, USA; and AMS Biotechnology Ltd., UK. Suitable derivatives include those that are disclosed in Roberts, *Chitin Chemistry*, MacMillan Press Ltd., London (1992).

The most preferred type of chitosan for use in the present invention is chitosan glutamate having a degree of deacetylation in the range of about 80 to 90% and a molecular weight in the range of about 300,000 to 600,000 Da (e.g. PROTASAN™ UPG213 (NovaMatrix)).

The chitosan or derivative thereof or salt of chitosan or salt of a derivative of chitosan used in this invention is used in the form of a finely divided powder. Suitable powders can be prepared by any appropriate method known in the art. Preferred methods for preparing the powder include milling and/or spray drying.

The preferred particle size of the chitosan or derivative thereof or salt of chitosan or salt of a derivative of chitosan used in the present invention is as defined above for the protein powder.

Most preferably, the formulations of the invention comprise chitosan glutamate having a mean particle size, expressed as the volume mean diameter ($D_{50\%}$), of about 25 to 200 Mm.

Preferred formulations of the invention comprise about 30 to 65% by weight of chitosan glutamate and about 15 to 65% by weight of protein.

The formulations of the present invention optionally contain small quantities of one or more additional water-soluble, non-gel forming ingredients in order to optimize powder properties, such as homogeneity or flow characteristics. By "non-gel forming", we mean an ingredient that, when placed in contact with water, does not form a gelatinous solid or semi-solid mass. Suitable additional ingredients include, but are not limited to, sugars such as sucrose and trehalose; polyols such as mannitol and sorbitol; and surfactants such as polysorbates; amino acids such as glycine; and polyethylene glycol. Mannitol is a preferred additional ingredient. The total amount of additional ingredients may be up to a total of about 20% by weight of the powder formulation. The particle size of such additives is preferably as defined above for the protein powder.

For avoidance of doubt, the powder formulations of the present invention may contain additional ingredients such as mannitol as a component of the dry protein powder and/or as a separate component of the formulation.

Given the complex structure of large proteins and their susceptibility to denaturation if handled inappropriately, it is important in preparing an intranasal powder formulation that the processing steps are kept to a minimum in order to preserve the integrity and biological activity of the protein.

The preferred process for preparing the formulations of the invention is by blending powder ingredients. In this process, a powder comprising a protein and optionally one or more additives as described above, a powder of chitosan or a derivative thereof or a salt of chitosan or a salt of a derivative of chitosan and any other powder ingredients are mixed together to form a uniform blend.

If the protein-containing powder is produced by freeze drying, its particle size is likely to, be heterogeneous and poorly defined. Therefore, prior to preparing the intranasal formulation, the protein powder will preferably undergo a process to produce particles of a well-defined size. Methods for reduction of particle size are well known to those skilled in the art. Preferred methods for reducing the size of the protein powder include milling. The particle size can be controlled using standard techniques such as sieving.

To minimize protein degradation, size reduction is preferably performed using low shear forces and/or at a low temperature. There are numerous types of mills available, and these are widely described in literature references, such as in J. T. Carstensen, *Pharmaceutical Principles of Solid Dosage Forms*, Chapter 2, Technomic, Lancaster, Pa. (1993); and Remington, *The Science and Practice of Pharmacy,* 20*th Edition*, Chapter 37, Lipincott, Williams and Wilkins, Baltimore (2000).

For preparing a uniform powder blend on a small scale, a pestle and mortar and/or sieve may be appropriate, whereas mechanical mixers are required for larger scale manufacture. There are numerous types of mixer available and these are widely described in the literature, for example Remington, *The Science and Practice of Pharmacy,* 20*th Edition*, Chapter 37, Lipincott, Williams and Wilkins, Baltimore (2000).

Alternative processes for preparing the formulations of the invention include spray drying, granulation and supercritical fluid processes.

In a spray drying process, an aqueous solution containing chitosan or a derivative thereof or a salt of chitosan or a salt of a derivative of chitosan, the protein and any other appropriate ingredients is sprayed into a current of hot air which results in rapid evaporation of the water to produce a powder. Further details on spray drying of pharmaceuticals may be found in Broadhead et al., *Drug Dev. Ind. Pharm.,* 18:1169-1206 (1992).

In a granulation process, a solution of a binding agent in an aqueous or organic solvent (the granulating solvent) is mixed into the protein, chitosan or derivative thereof or salt of chitosan or salt of a derivative of chitosan and any other appropriate ingredients to form a homogeneous mass. The mass is passed through a coarse mesh and the aqueous or organic solvent removed by evaporation/drying to produce granules. The granules may then, if required, be further milled and sieved to produce particles of the desired size. Although the binding agent is typically dissolved in the granulating solvent, alternatively it may added in dry form to a powder mixture and the solvent added to the powder blend to form the homogeneous mass. Further details on granulation processes may be found in the literature, for example J. T. Carstensen, *Pharmaceutical Principles of Solid Dosage Forms*, Chapter 6, Technomic, Lancaster, Pa. (1993). Hence, if a granulation process is used, the compositions may additionally comprise a binding (or granulating) agent. Such an agent is preferably used in an amount not exceeding about 3% by weight of the final-intranasal powder composition. Binding agents suitable for use in pharmaceutical products can be found in publications, such as *Handbook of Pharmaceutical Excipients,* 4*th edition*, Rowe et al. (eds.), Pharmaceutical Press, London (2003) and include celluloses, starches, sugars, gelatin and, preferably, polyvinylpyrrolidone (povidone).

Alternatively, an intranasal powder formulation could be prepared by firstly preparing granules from for example lyophilized protein. These granules can then be blended with chitosan or a derivative thereof or a salt of chitosan or a salt of a derivative of chitosan, and optionally any other appropriate ingredients, in powder or granule form to form a formulation of the present invention.

Supercritical fluid processes exploit the unique properties of supercritical fluids, such as carbon dioxide (Winters et al., *J. Pharm. Sci.*, 85:586-594 (1996); Subramaniam et al., *J. Pharm. Sci.*, 86:885-890 (1997); Palakodaty and York, *Pharm. Res.*, 16:976-985 (1999)). For example, in one type of process one or more of the ingredients of the formulations may be dissolved in a supercritical fluid, the fluid then allowed to rapidly expand and evaporate to leave particles. In another type of process, a supercritical fluid is mixed with a solution comprising one or more ingredients of the formulation such that addition of the supercritical fluid results in precipitation of the ingredients in the form of particles.

The formulations of the invention preferably have a particle size in the range of about 10 to 900 μm, more preferably about 10 to 600 μm and most preferably about 10 to 300 μm. More specifically, the mean particle size, expressed as the volume mean diameter ($D_{50\%}$) and measured by a technique such as light microscopy combined with image analysis lies within these ranges. The $D_{50\%}$ is preferably about 25 to 700 μm, more preferably about 25 to 450 μm and most preferably about 25 to 200 μm. Furthermore, no more than about 10% by volume of the particles have a diameter ($D_{10\%}$) less than 10 μm and at least about 90% by volume of the particles have a diameter ($D_{90\%}$) that does not exceed the upper limit of the size range.

It is desirable that the formulations of the invention do not contain substantial numbers of particles having a size below about 10 μm in order to minimize the possibility of delivery into the lungs.

In a preferred aspect of the present invention the protein is human growth hormone (hGH). Thus, the present invention specifically provides a powder formulation comprising hGH and chitosan or a derivative thereof or a salt of chitosan or a salt of a derivative of chitosan. hGH has, until now, had to be administered by subcutaneous or intramuscular injection due to poor absorption from other routes of administration. It would be advantageous to administer hGH by a non-injected route in order to improve patient acceptability, compliance and convenience.

We have surprisingly found that hGH can be effectively absorbed following intranasal administration of the hGH containing formulations of the present invention.

Naturally occurring human growth hormone (somatotropin) is secreted by the anterior lobe of the pituitary and is a heterogeneous mixture of proteins.

The principal form of human growth hormone is a single polypeptide chain of 191 amino acid residues with a molecular mass of 22 kDA. It promotes growth of skeletal, muscular and other tissues, stimulates protein anabolism, and affects fat and mineral metabolism (Goodman and Gilman's *The Pharmacological Basis of Therapeutics*, 9<sup>th</sup> Ed, McGraw-Hill, New York (1995)).

Synthetic human growth hormone (somatropin) is manufactured by recombinant DNA technology and is a 191 amino acid polypeptide (MW 22 kDa) with an amino acid sequence and two internal disulfide bridges identical to that of the major component of human pituitary growth hormone. An alternative form of hGH used in medicine is somatrem, which is an analogue of somatropin containing an additional methionyl amino acid residue (also termed methionyl-hGH).

By the term "human growth hormone" or "hGH" we mean naturally occurring somatotropin, synthetic somatropin and analogues such as somatrem.

Synthetic hGH is conventionally manufactured by recombinant DNA technology and is typically isolated and purified as an aqueous solution. In the present invention, the hGH is used in the form of a powder. hGH powders may be formed from the solutions using any suitable method known in the art such as those described above.

The hGH can be dried alone or, to improve stability, in the presence of an additive. Suitable additives are described above. It is preferable to dry the hGH in the presence of an additive.

The preferred means for isolating hGH in the form of a powder is freeze-drying from solution in a buffer, which optionally comprises mannitol and/or glycine.

The dry hGH powder obtained by these methods comprises at least about 40% by weight, preferably at least about 50%, more preferably at least about 60% and most preferably at least about 70% by weight of hGH.

Most preferably, the hGH powder is obtained by freeze-drying and comprises at least about 70% by weight of hGH and has a mean particle size, expressed as the volume mean diameter ($D_{50\%}$), of about 25 to 200 μm.

The hGH containing formulations of the present invention contain chitosan or a derivative thereof or a salt of chitosan or a salt of a derivative of chitosan, which is as defined above. Preferably, the hGH containing formulations contain chitosan glutamate.

The hGH containing formulations of the present invention preferably contain chitosan or a derivative thereof or a salt of chitosan or a salt of a derivative of chitosan in an amount of about 20 to 80% by weight, more preferably about 25 to 70% by weight and most preferably about 30 to 65% by weight.

Most preferably, the hGH containing formulations of the present invention contain chitosan glutamate with a mean particle size, expressed as the volume mean diameter ($D_{50\%}$), of about 25 to 200 μm.

The remainder of the powder formulation comprises hGH and, optionally, up to about 20% of additional ingredients to improve product stability and/or handling properties, such as powder flow. The hGH content of the powder formulation is preferably about 15 to 75% by weight, more preferably about 25 to 70% and most preferably about 30 to 65%.

The hGH containing formulations of the present invention may optionally contain one or more additional ingredients. Suitable additional ingredients include, but are not limited to, those listed above. Mannitol is a preferred additional ingredient.

A preferred hGH containing powder formulation of the present invention comprises about 30 to 65% by weight of chitosan glutamate, about 65 to 30% by weight of hGH and up to about 10% by weight of mannitol.

The hGH containing powder formulations can be made by the methods described above.

When the hGH containing formulation is prepared by a granulation process, a preferred binding agent for the hGH powder formulation is polyvinylpyrrolidone (PVP, povidone) and a preferred granulating solvent is dichloromethane (methylene chloride).

The particle size of the particles in the hGH containing formulations, regardless of the method by which they are made, is preferably about 10 to 900 μm, more preferably about 10 to 600 μm, and most preferably about 10 to 300 μm. More specifically, the mean particle size, expressed as the volume mean diameter ($D_{50\%}$) and measured by a technique such as light microscopy combined with image analysis lies within these ranges. The $D_{50\%}$ is preferably about 25 to 700 μm, more preferably about 25 to 450 μm and most preferably about 25 to 200 μm. Furthermore, no more than about 10% by volume of the particles have a diameter ($D_{10\%}$) less than 10 µm and at least about 90% by volume of the particles have a diameter ($D_{90\%}$) that does not exceed the upper limit of the size range.

Any suitable delivery device can be used to administer the formulations of the present invention to a patient. In order to ensure that the maximum surface area of the absorptive tissue of the nasal cavity is exposed to drug, the powder is preferably administered in aerosolized form i.e. a well dispersed plume of protein and chitosan particles. Preferred devices are those of a type where energy from patient inhalation (sniffing) is used to aerosolize the powder into the nasal cavity or where the device itself provides the aerosolization energy, such as via compressed air. An example of the former type of device is manufactured by Pfeiffer GmbH, Germany and an example of the latter type is the "Monopowder" manufactured by Valois SA, France.

The formulations of the invention may be used to treat/prevent diseases/conditions in mammalian patients depending upon the proteins which is/are employed. For the above, non-exhaustive, lists of drugs, diseases/conditions which may be mentioned including those against which the proteins in question are known to be effective, include those specifically listed for the proteins in question in Martindale, *The Extra Pharmacopoeia*, 33rd Edition, Royal Pharmaceutical Society, London (2002).

For example, in human medicine, hGH is administered to children to treat growth retardation, for example short stature due to insufficient growth hormone secretion, Turner's syndrome or chronic renal insufficiency. In adults it is used as a treatment for growth hormone deficiency and for control of HIV-related wasting and cachexia. The hGH-containing formulations of the present invention can be used for these purposes.

The present invention provides a method of treating or preventing growth retardation, such as that caused by insufficient growth hormone secretion, Turner's syndrome or chronic renal insufficiency; growth hormone deficiency; or for the control of HIV-related wasting and cachexia which comprises the intranasal administration of an hGH-containing composition as defined above to a patient.

Formulations of the invention have the advantage that they may provide enhanced absorption of proteins that are not typically well absorbed when administered via the nasal route following administration.

Additionally, it has been found that the powder formulations of the present invention have improved storage stability compared to aqueous solutions containing the same components.

Example 1

Preparation of Nasal Solution Containing 20 mg/ml hGH 5 ml of recombinant hGH bulk solution (10 mg/ml hGH and 2 mg/ml phosphate buffer salt, Biochemie, Kundl, Austria) was dispensed into a 20-ml glass vial. The vial contents were frozen using liquid nitrogen and freeze-dried for 48 hours using a Thermo Savant Modulyo D freeze dryer (Thermo Life Sciences, UK). A nasal solution containing 20 mg/ml hGH was prepared by adding 2.5 ml of water to the vial.

Example 2

Preparation of Nasal Solution Containing 20 mg/ml hGH and 5 mg/ml Chitosan Glutamate 50 ml of 10 mg/ml hGH bulk solution was transferred into a 250 ml flask, frozen using liquid nitrogen and freeze dried for 48 hours, as described in Example 1. The freeze-dried powder was transferred into a glass vial, which was sealed and stored refrigerated until required. To prepare a sample of the nasal formulation, 25 mg of chitosan glutamate (Protasan UPG213, FMC Biopolymer, Norway) was weighed into a 5 ml volumetric flask. 120 mg of the freeze-dried hGH powder (=100 mg hGH and 20 mg of phosphate buffer salt) was weighed into a 50 ml beaker and 2 ml of water added. The hGH solution was transferred to the flask containing chitosan glutamate. The beaker was rinsed with 2×1 ml aliquots of water which were added to the flask. 0.1 ml of 1 M hydrochloric acid (BDH, Poole, UK) was added to the flask and the contents stirred until a turbid solution had formed. The pH of the solution was checked and, if required, additional 1 M hydrochloric acid added to adjust the solution to pH 4. The solution was then made up to 5 ml with water.

Example 3

Preparation of hGH/chitosan Glutamate Nasal Powder (35.5% w/w hGH)

20 ml of 10 mg/ml hGH bulk solution was transferred into a 100 ml flask, frozen using liquid nitrogen and freeze dried for 48 hours. 323 mg of chitosan glutamate was transferred to a mortar and the freeze-dried hGH powder was added and carefully mixed using a pestle. The powder mixture was transferred into a 20 ml glass vial, which was sealed and placed into a Turbula T2C mixer (Willy Bachofen, Basel, Switzerland). The vial contents were mixed at speed setting 3 for 10 minutes. The final product was stored at 4° C until required and comprised 35.5% w/w hGH, 7.1% w/w phosphate buffer salts and 57.4% w/w chitosan glutamate.

Example 4

Preparation of hGH/chitosan Glutamate/mannitol Nasal Powder (35.5% w/w hGH)

20 ml of 10 mg/ml hGH bulk solution was transferred into a 100 ml flask. 200 mg of mannitol (Fisher Scientific, Loughborough, UK) was dissolved by gentle agitation in the hGH solution. The flask contents were frozen using liquid nitrogen and freeze dried for 48 hours. 123 mg of chitosan glutamate was transferred to a mortar and the freeze-dried hGH/mannitol powder was added and carefully mixed using a pestle. The powder mixture was transferred into a 20 ml glass vial, which was sealed and placed into a Turbula T2C mixer. The vial contents were mixed at speed setting 3 for 10 minutes. The final product was stored at 4° C. until required and comprised 35.5% w/w hGH, 7.1% w/w phosphate buffer salts, 35.5% w/w mannitol and 21.9% w/w chitosan glutamate.

Example 5

Preparation of Subcutaneous Solution Containing 0.57 mg/ml hGH 10 mM phosphate buffer, pH 7 was prepared by dissolving 112 mg of disodium hydrogen phosphate dihydrate (Fisher Scientific) and 57 mg of sodium dihydrogen phosphate dihydrate (Fisher Scientific) in 95 ml of water and then making up to 100 ml with water. 2.85 ml of 10 mg/ml hGH bulk solution was measured into a 50 ml volumetric flask and made up to volume with the 10 mM buffer. In a laminar flow cabinet 20 ml of the solution was passed through a sterilizing filter (0.2 urn) into each of two 50 ml sterile injection vials which were stoppered and capped. The vials were stored at 4° C. until required.

Example 6

Pharmacokinetic Evaluation of Formulations Prepared in Examples 1-5

The pharmacokinetic performance of the hGH preparations described in Examples 1-5 was evaluated in sheep. The four intranasal formulations and the subcutaneous injection were administered to a group of five animals, weighing in the range 60-70 kg, following a randomized crossover design.

The intranasal formulations were administered at a hGH dose of 17 mg and the subcutaneous injection was administered at a hGH dose of 1.7 mg.

Nasal liquid doses were administered using a spray device inserted a few centimeters into the sheep nostril. Nasal powder doses were weighed into an oral/tracheal tube. The tube was inserted a few centimeters into the nostril and the contents puffed into the nasal cavity using a bellows attached to the end of the tube. Doses were divided equally between both nostrils.

Blood samples were collected and serum separated. The serum was analyzed by immunometric assay (IMMULITE® 2000 Growth Hormone kit, Diagnostic Products Corporation, Los Angeles, USA) for hGH content. Pharmacokinetic parameters were calculated from the serum data.

Mean serum concentration vs. time curves are shown in FIG. 1. A summary of the pharmacokinetic parameters is provided in the table below (mean n=5, standard deviation).

| Formulation | Mean $t_{max}$ (min) | Mean $C_{max}$ (ng/ml) | Mean bioavailability relative to s/c injection (%) |
|---|---|---|---|
| Intranasal chitosan solution | 75 ± 24 | 22.8 ± 14 | 3.6 ± 2.5 |
| Intranasal chitosan powder | 78 ± 16 | 53.5 ± 33.2 | 7.1 ± 4.5 |
| Intranasal chitosan powder with mannitol | 69 ± 20 | 45.7 ± 23.0 | 6.0 ± 3.2 |
| Intranasal control solution | 41 ± 14 | 1.3 ± 0.3 | 0.2 ± 0.05 |
| Subcutaneous injection | 150 ± 60 | 10.8 ± 1.3 | [100] |

The absorption of hGH from the nasal control solution was negligible.

The chitosan solution formulation produced a large increase in hGH bioavailability. However, this formulation was found to have poor stability, with the appearance of a precipitate after only a short period of storage.

The powder formulations provided the highest intranasal absorption of hGH. Inclusion of mannitol did not adversely affect hGH absorption.

Hence, if required to optimize powder properties, it would be feasible to include mannitol in the hGH formulation without compromising bioavailability.

Example 7

Preparation of hGH Powder 170 ml of recombinant hGH bulk solution (8.8 mg/ml hGH and 2 mg/ml phosphate buffer salt, Biochemie, Kundl, Austria) was transferred into a 1000 ml glass beaker and frozen by immersing the beaker in liquid nitrogen. The frozen hGH solution was transferred to a freeze dryer and dried for a period of 48 hours. The dried product was passed through a 0.85 mm sieve (Endecotts, London, UK) and stored in a sealed glass jar at 4° C. until required.

Example 8

Preparation of hG}I/chitosan Glutamate Powder Blend (50% w/w hGH)

648 mg of the sieved freeze dried hGH powder (prepared in Example 7) and 408 mg of chitosan glutamate (Protasan UPG213, FMC Biopolymer, Norway) were weighed into a mortar and gently and carefuilly mixed with a pestle. The powder mixture was transferred into a glass vial, which was sealed and placed into a Turbula T2C mixer. The vial contents were mixed at speed setting 2 for 30 minutes. The final product was stored at 4° C. until required and comprised 50.0% w/w hGH, 11.4% w/w buffer salt and 38.6% w/w chitosan glutamate.

Example 9

Selection of Granulating Solvent 10 mg samples of freeze-dried hGH powder (prepared as described in Example 7) were weighed into each of three 10 ml glass vials. To one vial was added 1 ml of propan-2-ol (Fisher Scientific), to the second vial was added 1 ml of ethanol (Fisher Scientific) and to the third vial was added 1 ml of dichloromethane (Fisher Scientific). The vials were agitated to disperse the contents and placed in a fume cupboard for one hour to allow most of the solvent to evaporate. The vials were then transferred to an oven set at 40° C. for 2 hours to remove any remaining solvent. Finally, 5 ml of water was added to each vial and the vial contents gently stirred for 30 minutes. The samples in which the hGH had been exposed to ethanol and propan-2-ol were both cloudy solutions indicating aggregation/denaturation of the protein had occurred. The hGH samples which had been exposed to dichloromethane formed a clear solution. The integrity of hGH in this sample was also confirmed by size exclusion HPLC analysis (BioSep SEC2000 300×7.8 mm column [Phenomenex, Macclesfield, UK], pH 7.2 phosphate buffer mobile phase, 0.3 ml/min flow rate, UV detection at 214 nm). On the basis of these results dichloromethane was selected as the solvent for preparing a hGH granule formulation.

Example 10

Preparation of hGH/chitosan Glutamate Granules (50% w/w hGH)

15 mg of polyvinylpyrrolidone (PVP) (Kollidon 30, BASF Pharma, Germany) was weighed into a 100 ml glass beaker and 3 ml of dichloromethane (Fisher Scientific, Loughborough, UK) added. The beaker contents were agitated to dissolve the PVP. 864 mg of the sieved freeze dried hGH powder (prepared in Example 7) and 529 mg of chitosan glutamate were weighed and added to the beaker containing PVP solution. The beaker contents were thoroughly mixed with a spatula and the majority of the solvent allowed to evaporate in a fume cupboard. The mixture was passed through a 0.25 mm sieve (Endecotts) and transferred into a tared 50 ml glass beaker. The beaker was placed into an oven set at 40° C. and removed and re-weighed at 30-minute intervals until the weight was stable i.e. all solvent had evaporated. The dried granules were then passed through a 0.15 mm sieve (Endecotts). Any larger granules were gently milled using a pestle and mortar until they were of a size that would pass through the sieve. The final product was stored in a sealed glass vial at 4° C. until required and comprised 50.0% w/w hGH, 11.4% w/w buffer salt, 37.5% w/w chitosan glutamate and 1.1% w/w PVP.

Example 11

Preparation of Subcutaneous Solution Containing 0.57 mg/ml hGH 10 mM phosphate buffer, pH 7 was prepared by dissolving 56 mg of disodium hydrogen phosphate dihydrate (Fisher Scientific) and 29 mg of sodium dihydrogen phosphate dihydrate (Fisher Scientific) in 45 ml of water and then making up to 50 ml with water. 1.62 ml of 8.8 mg/ml hGH bulk solution was measured into a 25 ml volumetric flask and made up to volume with the 10 mM buffer. In a laminar flow cabinet 20 ml of the solution was passed through a sterilizing filter (0.2 urn) into a 50 ml sterile injection vial which was stoppered and capped. The vial was stored at 4° C. until required.

Example 12

Pharmacokinetic Evaluation of Formulations Prepared in Examples 8, 10 and 11

The pharmacokinetic performance of the hGH preparations described in Examples 8, 10 and 11 was evaluated in sheep. The two intranasal formulations and the subcutaneous injection were administered to a group of six animals, weighing in the range 50-60 kg, following a randomized crossover design. The intranasal formulations were administered at a nominal hGH dose of 17 mg (powder dose weight 34 mg). The subcutaneous injection was administered at a nominal hGH dose of 1.7 mg (volume administered 3.0 ml).

Figure 2:
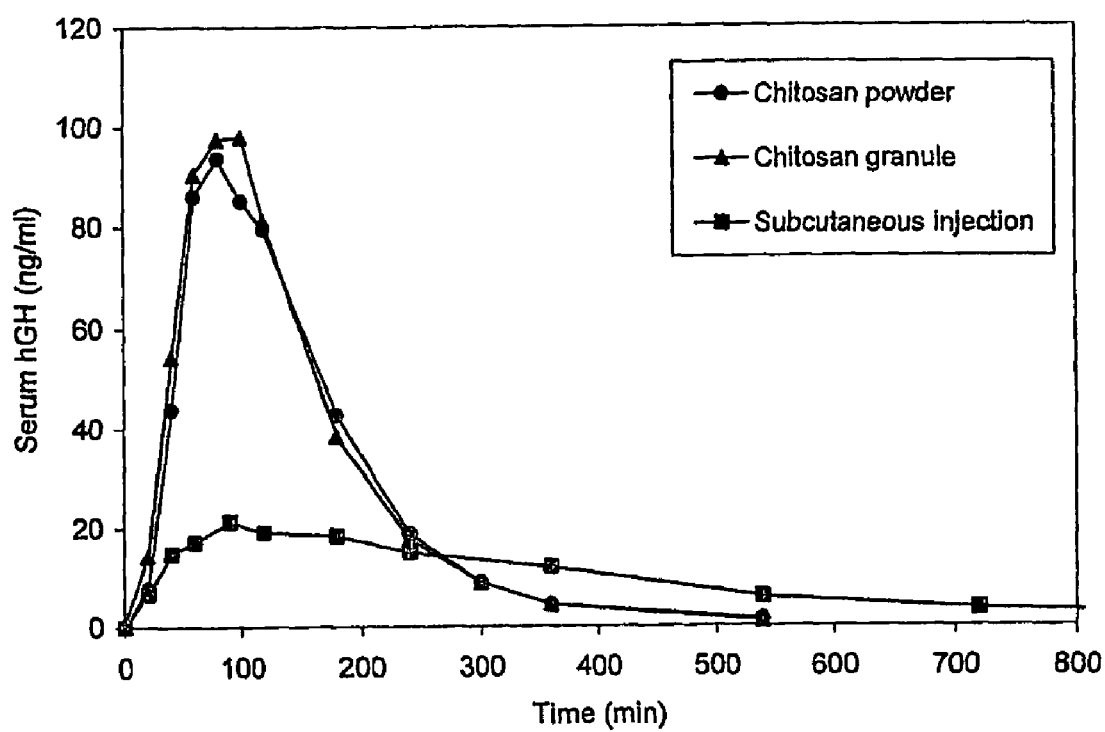
FIG. 2 is a graph showing mean hGH serum concentration vs. time curves following intranasal administration of powder and granule formulations (obtained by way of Example 12) to sheep (mean, n=6)

Blood samples were collected and serum separated. The serum was analyzed by immunometric assay for hGH content. Pharmacokinetic parameters were calculated from the serum data. Mean serum concentration vs. time curves are shown in FIG. 2. A summary of the pharmacokinetic parameters is provided in the table below (mean n=6, ± standard deviation).

| Formulation | Mean $t_{max}$ (min) | Mean $C_{max}$ (ng/ml) | Mean bioavailability relative to s/c injection (%) |
|---|---|---|---|
| Intranasal hGH/chitosan powder blend | 90 ± 17 | 98 ± 58 | 14 ± 9 |
| Intranasal hGH/chitosan granuales | 73 ± 16 | 106 ± 47 | 15 ± 8 |
| Subcutaneous injection | 110 ± 41 | 22 ± 1 | [100] |

The bioavailability of intranasal hGH was further improved compared to Examples 3 and 4. This improvement is attributed in part to the, introduction of a manufacturing step to control the particle size of the powders. Formulating hGH into a granule had no effect on bioavailablity.

Example 13

Performance of Powders Filled into Nasal Spray Device

A 10 mg sample of the powder formulation prepared in Example 8 was filled into a Monopowder nasal spray device (Valois, Marly-le-Roi, France). A sample of the powder formulation prepared in Example 8 was further milled in a mortar and passed through a 0.25 mm sieve. 10 mg of this sieved powder was filled into a Monopowder device. Each device was actuated in a vertical orientation and the emission of powder captured on a video camera. A single image of each device, corresponding to the maximum extent of powder dispersion after leaving the device is shown in FIG. 3.

Figure 3A:
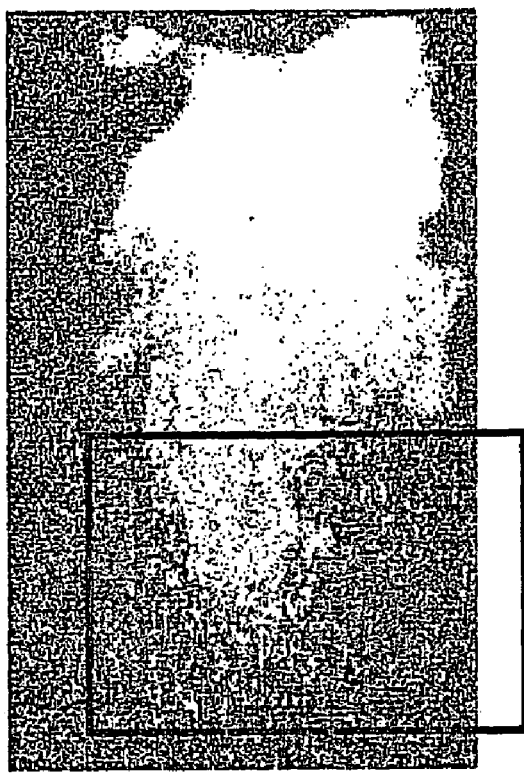
FIG. 3A is a video image of the plume of hGH/chitosan powder obtained when the powder prepared by way of Example 8 was dispersed using a Monopowder device, as in Example 13. The boxed region shows the population of larger particles falling back towards the device.
Figure 3B:
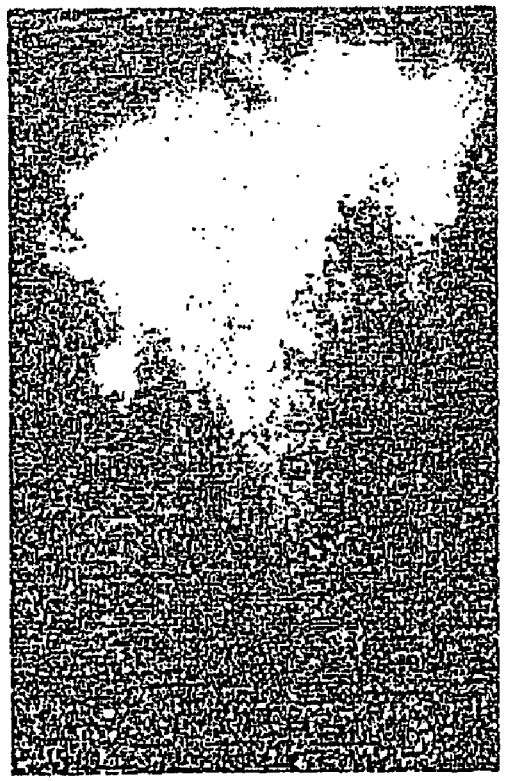
FIG. 3B is a video image of the plume of hGH/chitosan powder obtained when the powder prepared by way of Example 8 and passed through a 0.25 mm sieve was dispersed using a Monopowder device, as in Example 13.

FIG. 3A shows the plume of powder for the powder prepared in Example 8, in which the only sieving step was passing the hGH through a 0.85 mm sieve. FIG. 3B shows the plume of powder for the formulation that had been passed through a 0.25 mm sieve. In FIG. 3A there is a population of particles at the bottom of the plume of powder that are beginning to fall back towards the device. These are presumed to be primarily hGH particles, which only underwent a coarse sieving process. The powder plume in FIG. 3B appears to be more uniform with an absence of a population of larger particles. Hence, it is advantageous to sieve the hGH/chitosan intranasal powder formulation to a small particle size to ensure uniform deposition and distribution of the formulation components in the nasal cavity.

Example 14

Preparation of hGH/chitosan Powder Blend Containing 64% w/w hGH 20 ml of hGH bulk solution was freeze dried (as described in Example 7) and passed through a 0.85 mm sieve. The sieved hGH was mixed with 61 mg of chitosan glutamate using a mortar and pestle and collected in a vial. The mixture was further blended using a Turbula T2C mixer at speed setting 2 for 30 minutes. The final product comprised 64% w/w hGH, 14% w/w buffer salt and 22% chitosan glutamate.

Example 15

Preparation of hGH/chitosan/PVP Granules Containing 64% w/w hGH 50 ml of hGH bulk solution was freeze dried (as described in Example 7 but omitting sieving step). The unsieved hGH and 147 mg of chitosan glutamate were added to a solution comprising 5 mg of PVP dissolved in 1-2 ml of dichloromethane in a beaker, then mixed thoroughly with a spatula to form a homogeneous mixture. The majority of the dichloromethane was evaporated in a fume cupboard and the mixture was passed through a 0.25 mm sieve to produce granules. The granules were dried at 40° C. in an oven to remove the remaining dichloromethane. The dry granules were passed through a 0.15 mm sieve and collected in a vial. The final product comprised 64% w/w hGH, 14% w/w buffer salt, 21% chitosan glutamate and 1% w/w PVP.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A powder formulation for intranasal delivery consisting essentially of a protein having a molecular weight of 10 kDa or greater; chitosan glutamate in an amount of 30 to 65% by weight based on the total weight of the formulation; and optionally one or more additional water-soluble, non-gel forming ingredients, wherein the protein is in the form of a protein powder having a mean particle size, expressed as the volume mean diameter ($D_{50\%}$), of about 25 to 200 μm, and the chitosan glutamate is in the form of a powder having a mean particle size, expressed as the volume mean diameter ($D_{50\%}$), of about 25 to 200 μm and has a solubility in water of at least 10 mg/ml at room temperature and atmospheric pressure.

2. The formulation according to claim 1, comprising about 15 to 65% by weight of the protein based on the total weight of the formulation.

3. The formulation according to claim 1, further comprising mannitol.

4. The formulation according to claim 3, comprising up to 10% by weight mannitol based on the total weight of the formulation.

5. The formulation according to claim 1, wherein the protein is one that is absorbed into systemic circulation through nasal mucosa and that has a direct and/or systemic biological effect following absorption.

6. A powder formulation for intranasal delivery consisting essentially of human growth hormone; chitosan or a derivative thereof or a salt of chitosan or a salt of a derivative of chitosan; and optionally one or more additional water-soluble, non-gel forming ingredients, wherein the chitosan, the derivative thereof, the salt of chitosan or the salt of a derivative of chitosan is water soluble, having a solubility in water of at least 10 mg/ml at room temperature and atmospheric pressure, and is in the form of a powder having a mean particle size, expressed as the volume mean diameter ($D_{50\%}$), of about 25 to 200 μm, and the human growth hormone is in the form of a protein powder having a mean particle size, expressed as the volume mean diameter ($D_{50\%}$), of about 25 to 200 μm.

7. The formulation according to claim 6, comprising chitosan glutamate.

8. The formulation according to claim 7, comprising about 30 to 65% by weight chitosan glutamate based on the total weight of the formulation.

9. The formulation according to claim 6, comprising about 15 to 65% by weight of human growth hormone based on the total weight of the formulation.

10. The formulation according to claim 6, further comprising mannitol.

11. The formulation according to claim 10, comprising up to 10% by weight mannitol based on the total weight of the formulation.

12. The formulation according to claim 6, comprising about 30 to 65% by weight of human growth hormone based on the total weight of the formulation.

13. A process for preparing a formulation according to claim 1, which process comprises mixing the protein powder, the powder of chitosan glutamate and optionally a powder of the one or more additional water-soluble, non-gel forming ingredients to produce a uniform blend.

14. The process according to claim 13, wherein the protein powder comprises at least 60% by weight of protein based on the total weight of the protein powder.

15. The process according to claim 14, wherein the protein powder comprises at least 70% by weight of human growth hormone based on the total weight of the protein powder.

16. The process according to claim 13, wherein the protein powder is prepared by freeze-drying a buffered solution comprising the protein and optionally an additive, and the freeze-dried powder is optionally subjected to a milling and/or sieving step prior to being mixed with the other powders.

17. A method of enhancing intranasal absorption of a protein having a molecular weight of at least 10 kDa, comprising administering the protein intranasally with chitosan glutamate in a powder formulation, wherein the powder formulation consists essentially of the protein; about 30 to 65% by weight chitosan glutamate based on the total weight of the formulation; and optionally one or more additional water-soluble, non-gel forming ingredients, wherein the protein is in the form of a protein powder having a mean particle size, expressed as the volume mean diameter ($D_{50\%}$), of about 25 to 200 μm, and the chitosan glutamate is in the form of a powder having a mean particle size, expressed as the volume mean diameter ($D_{50\%}$), of about 25 to 200 μm and has a solubility in water of at least 10 mg/ml at room temperature and atmospheric pressure.

18. A method of enhancing intranasal absorption of human growth hormone, comprising administering the human growth hormone intranasally with chitosan or a derivative thereof or a salt of chitosan or a salt of a derivative of chitosan in a powder formulation, wherein the powder formulation consists essentially of the human growth hormone; chitosan or a derivative thereof or a salt of chitosan or a salt of a derivative of chitosan; and optionally one or more additional water-soluble, non-gel forming ingredients, wherein the chitosan, the derivative thereof, the salt of chitosan or the salt of a derivative of chitosan is water soluble, having a solubility in water of at least 10 mg/ml at room temperature and atmospheric pressure, and is in the form of a powder having a mean particle size, expressed as the volume mean diameter ($D_{50\%}$), of about 25 to 200 μm, and the human growth hormone is in the form of a protein powder having a mean particle size, expressed as the volume mean diameter ($D_{50\%}$), of about 25 to 200 μm.

19. A method for treatment or prevention of growth retardation, growth hormone deficiency or for the control of HIV-related wasting and cachexia, comprising intranasally administering a human growth hormone containing powder formulation, wherein the powder formulation consists essentially of the human growth hormone; chitosan or a derivative thereof or a salt of chitosan or a salt of a derivative of chitosan; and optionally one or more additional water-soluble, non-gel forming ingredients, wherein the chitosan, the derivative thereof, the salt of chitosan or the salt of a derivative of chitosan is water soluble, having a solubility in water of at least 10 mg/mi at room temperature and atmospheric pressure, and is in the form of a powder having a mean particle size, expressed as the volume mean diameter ($D_{50\%}$), of about 25 to 200 μm, and the human growth hormone is in the form of a protein powder having a mean particle size, expressed as the volume mean diameter ($D_{50\%}$), of about 25 to 200 μm.

20. The method according to claim 19, wherein the growth retardation is caused by insufficient growth hormone secretion, Turner's syndrome or chronic renal insufficiency.

21. A method of administering a protein to a patient, the method comprising intranasally administering the formulation according to claim 1.

22. A nasal delivery device or a dose cartridge for use in a nasal delivery device comprising a formulation according to claim 1.

23. The nasal delivery device or the dose cartridge according to claim 22, comprising about 5 to 20 mg of the formulation.

* * * * *